United States Patent [19]

Damgaard-Iversen et al.

[11] Patent Number: 5,009,658

[45] Date of Patent: Apr. 23, 1991

[54] DUAL FREQUENCY LASER LITHOTRIPTER

[75] Inventors: Karsten Damgaard-Iversen, Marietta, Ga.; Robert C. Morris, Morris County, N.J.; Timothy C. Chin, Hunterdon County, N.J.; Jerry W. Kuper, Somerset County, N.J.

[73] Assignees: Karl Storz Endoscopy-America, Inc., Culver City, Calif.; Allied-Signal, Inc., Morris Township, Morris County, N.J.

[21] Appl. No.: 337,919

[22] Filed: Apr. 14, 1989

[51] Int. Cl.$^5$ .............................................. A61B 17/22
[52] U.S. Cl. ........................................... 606/128; 606/3
[58] Field of Search .................. 128/303.1, 328, 24 A, 128/24 AA, 24.1, 395, 398; 606/3, 15, 18, 127, 128

[56] References Cited

U.S. PATENT DOCUMENTS

| | | | |
|---|---|---|---|
| 4,391,275 | 7/1983 | Fankhauser et al. | 128/362 |
| 4,408,602 | 10/1983 | Nakajima | 606/18 |
| 4,672,969 | 6/1987 | Dew | 606/3 |
| 4,764,930 | 8/1988 | Bille et al. | 372/75 |
| 4,791,927 | 12/1988 | Menger | 128/303.1 |

FOREIGN PATENT DOCUMENTS

86/06269 11/1986 PCT Int'l Appl. .

OTHER PUBLICATIONS

"A Q-Switched Alexandrite Laser for Laser Induced Shock Wave Lithotripsy (LISL)-Basics and In Vitro Studies", European Laser Journal for Medicine and Surgery, E. Steiger and J. W. Kuper, 1988.
Topical Meeting on Tunable Solid State Lasers Technical Digest, "Medical Applications of Alexandrite Laser Systems", Oct., 1987, Kuper et al.
PCT/WIPO Publication #WO89/04147 based on PCT/US88/04000, Pub. Date May 18, 1989; Applicant, Filler, W. S., Title: ESWL Employing Non-Focused Spherical-Sector Shock Waves.

Primary Examiner—Ruth S. Smith
Assistant Examiner—Kevin Pontius
Attorney, Agent, or Firm—Louis T. Isaf

[57] ABSTRACT

Method and apparatus are provided for laser lithotripsy by subjecting calcified matter in the mammalian body, especially the human body, to two spatially and temporally overlapping pulsed laser light beams in the 300–450 and 600–900 nanometer wavelength range.

38 Claims, 6 Drawing Sheets

In-Vitro Lithotripsy Test Results: Candela Mdl-1 Laser Lithotripter (504 nm light & 250 um Fiber)

| Stone #: | Stone Composition: Interior | Exterior | Surface: | Color: | Pulse Energy: | Rep. Rate | Fragmentation Response: |
|---|---|---|---|---|---|---|---|
| KDI-6 | 95%-CaPO4 5%-Struvite | 85%-CaPO4 10%-CaOX(m) 5%-Struvite | Very Smooth | Light Beige | 40-50mj | 5&20 Hz | • Consistent Plasma Sparking<br>• Dust Like Particles |
| KI-VI | CaPO | CaOX | Very Smooth (Bladder) | White | 60mj | 5&20 Hz | • No Plasma Sparking<br>• No Fragmentation |
| KDI-5 | 60%-CaPO4 40%-Brushite | 65%-CaPO4 35%-Brushite | Smooth & Hard (Bladder) | Med. Beige | 60mj | 5&20 Hz | • Intermittent Plasma Spark.<br>• Little or No Fragmentation |
| KDI-8 | 70%-Brushite 25%-CaPO4 5%-CaOX(m) | 100%-Brushite | Smooth & Hard (Bladder) | Med. Beige | 60mj | 5&20 Hz | • No Plasma Sparking<br>• No Fragmentation |
| KI-XI | Apatit & Struvite | Apatit & Struvite | Porous (Staghorn) | White | 30&60mj | 5&20 Hz | • Occasional Plasma Sparking<br>• No Fragmentation |
| KI-XIII | Apatit & Struvite | Apatit & Struvite | Porous (Staghorn) | Brown Ext. White Int. | 30&60mj | 5&20 Hz | • No Sparking in White Areas<br>• Some Spark in Brown Areas<br>• No Fragmentation |
| KDI-28 | 100%-Uric Acid | 100%-Uric Acid | Very Smooth | Near White | 50&60mj | 5&20 Hz | • Plasma Sparking<br>• No Fragmentation |
| KDI-9 | 100%-Uric Acid | 100%-Uric Acid | Very Smooth | Light Beige | 60mj | 20Hz | • Good Plasma Sparking<br>• Drilling Effect<br>• Very Slow Rem. of Material |
| KI-III | Uric Acid | Uric Acid | Rough | Dark Ext. Beige Int. | 60mj | 20Hz | • Consistent Plasma Sparking<br>• Some Fragmentation–Slow |
| KI-IV | Uric Acid | CaOX | Smooth | Light Beige | 60mj | 20Hz | • Plasma Sparking<br>• Dust Like Particles |
| KI-XVI | Cystine | Cystine | Rough | Light Yellow | 60mj | 5&20 Hz | • No Plasma Sparking<br>• No Fragmentation |

FIG 6

Intro-Vitro Lithotrippsy Test Results: Dual Frequency SW/LW (378nm/755nm) Alexandrite Laser Lothotripter

| Stone #: | Stone Composition: Interior | Stone Composition: Exterior | Surface: | Color: | Pulse Energy UV: | Pulse Energy IR: | Fragmentation Response: |
|---|---|---|---|---|---|---|---|
| KDI-6 | 95%-CaPO4 5%-Struvite | 85%-CaPO4 10%-CaOX(m) 5%-Struvite | Very Smooth | Light Beige | 8mj | 15mj | • Consistent Plasma Sparking<br>• Very fast fragmentation<br>• 1-2mm particles |
| KI-VI | CaPO | CaOX | Very Smooth (Bladder) | White | 5mj | 45mj | • Consistent plasma sparking<br>• Ext. & Int. fragmentation |
| KDI-5 | 60%-CaPO4 40%-Brushite | 65%-CaPO4 35%-Brushite | Smooth&Hard (Bladder) | Med. Beige | 7mj | 52mj | • Consistent plasma sparking<br>• Good fragmentation (<1mm) |
| KDI-8 | 70%-Brushite 25%-CaPO4 5%-CaOX(m) | 100%-Brushite | Smooth&Hard (Bladder) | Med. Beige | 7mj | 52mj | • Consistent plasma sparking<br>• Little or no fragmentation in smooth surface layer |
| KI-XI | Apatit & Struvite | Apatit & Struvite | Porous (Staghorn) | White | 4mj | 40mj | • Consistent plasma sparking<br>• Good fragmentation |
| KI-XIII | Apatit & Struvite | Apatit & Struvite | Porous (Staghorn) | Brown Ext. White Int. | 4mj | 40mj | • Consistent plasma sparking in brown ext. & white int.<br>• Good fragmentation |
| KDI-28 | 100%-Uric Acid | 100%-Uric Acid | Very Smooth | Near White | 7mj | 52mj | • Consistent plasma sparking<br>• Very fine particles-slow |
| KDI-9 | 100%-Uric Acid | 100%-Uric Acid | Very Smooth | Light Beige | 7mj | 52mj | • Consistent plasma sparking<br>• Very fine fragments-slow |
| KI-III | Uric Acid | Uric Acid | Rough | Dark Ext. Beige Int. | 4mj | 40mj | • Consistent Plasma Sparking<br>• Some fragmentation |
| KI-IV | CaOX | CaOX | Smooth | Light Beige | 7mj | 52mj | • Consistent plasma sparking<br>• Some fragmentation |
| KI-XVI | Cystine | Cystine | Rough | Light Yellow | 4mj | 32mj | • Consistent plasma sparking<br>• Very good fragmentation |

Test conditions: 500-300um tapered fiber 6Hz repetition rate

FIG 7

DUAL FREQUENCY LASER LITHOTRIPTER

FIELD OF THE INVENTION

The present invention relates generally to laser lithotripsy, and more particularly to an improved laser lithotripter comprising a dual wavelength pulsed laser for fragmentation of calcified matter in the human body such as biliary and urinary calculi.

BACKGROUND OF THE INVENTION

One method of laser lithotripsy known in the art is that disclosed in PCT Publication No. WO 86/6269 of Furumoto et al. Furumoto discusses the use of a laser lithotripter delivering pulsed laser light at a single wavelength in the 350–550 nanometer (nm) range. Although Furumoto contemplates use of pulse energy levels in the range of 5 –200 millijoules (mJ), in practice the energy range for achieving effective fragmentation is in the order of 20–200 mJ. Furumoto's wavelength of 350 –550 nm lies within a range of significant energy absorption by water and hemoglobin, and thus poses risk of damage to the surrounding tissue during treatment. Further, while in its preferred embodiment operating at a wavelength of 504 nm and pulse energy levels of 30–60 mJ, this modality is effective for fragmentation of many urinary and biliary calculi, however, cystine stones, brushite stones, as well as certain calciumoxalate monohydrate and uric acid stones cannot be treated without the use of undesirably higher pulse energy levels and/or shorter wavelengths.

We have investigated the use of a Q-switched alexandrite laser lithotripter to address tissue damage concerns. In our experiments the laser lithotripter delivered pulsed laser light in the wavelength range of 730–780 nm, where the energy absorption by hemoglobin and water is significantly lower than in the 350–550 nm range. This lithotripter was capable of generating energy in the 0–300 mJ range; in practice, the energy range which is effective for stone fragmentation is in the order of 30–120 mJ. A detailed in vitro study of the Q-switched alexandrite laser lithotripter has disclosed that the energy threshold for achieving the plasma sparking at the surface of the targeted calculi, which is the driving force in the fragmentation process, is undesirably high for many stone compositions. By plasma sparking we mean the initiation of dielectric breakdown of the targeted material, a process which includes the emission of a bright flash of white light and the launching of an audible acoustic wave. Indeed, the pulse energy levels and associated peak power densities required to achieve plasma sparking in certain stone compositions exceeds the transmission capabilities of the fused silica fibers preferably used for clinical laser lithotripsy and generates violent forces which propel the calculi and its larger fragments away from the fiber tip. As a result of these phenomena the range of different compositions of calculi which can be effectively fragmented with the Q-switched alexandrite laser lithotripter is less than that obtainable with the Furumoto apparatus.

Laser apparatus have previously been employed for invasive surgery in the human body. For example, U.S. Pat. No. 4,791,927 to Menger describes a dual-wavelength laser scalpel for both cutting and coagulating tissue employing a laser beam in the wavelength range of 500–800 nm for cauterizing bleeding blood vessels through photocoagulation, and a laser bean in the wavelength range from 250–400 nm for cutting tissue by photoablation.

There is, accordingly, a need for an improved lithotripsy method and apparatus which mainly utilizes the laser light in the long (600–900 nm) wavelength range to effectively treat most urinary and biliary calculi and minimize the total laser pulse energy required to obtain effective stone fragmentation.

Accordingly, it is an object of the present invention to provide a method and related apparatus for improved effectiveness of laser lithotripsy.

Another object of the present invention is to provide an effective laser lithotripter which can fragment most calcified matter while exposing the calcified matter and surrounding tissue to minimum amounts of short wavelength light.

SUMMARY OF THE INVENTION

Briefly described, the present invention provides a method (and related apparatus) for fragmentation of calcified matter in the human body which method comprises the simultaneous irradiation of the calcified matter by pulsed coherent radiation at two separate wavelengths (short and long), (1) a short wavelength (SW) in the range of 300–450 nm, which acts as an igniter which initiates plasma sparking in the calculi; and (2) a long wavelength (LW) in the range of 600–900 nm, which is readily absorbed in the plasma generated by the short wavelength pulse and amplifies the plasma sparking, thus amplifying the the resultant fragmentation of the object calculi. The initially formed plasma thus acts as a black body absorber.

The short wavelength pulses are administered at a relatively lower energy of from about 2 to about 30 mJ, desirably at an energy level of from about 2 to about 16 mJ, and preferably at an energy level of from about 2 to about 12 mJ, at pulse duration of from about 50 to about 300 nanoseconds (ns), preferably of from about 75 to about 150 ns.

The long wavelength pulses are administered at an energy level of from about 15 to about 100 mJ, desirably at an energy level of from about 15 to about 75 mJ, and preferably at an energy level of from about 15 to about 60 mJ, at pulse duration of from about 50 to about 300 nanoseconds (ns), preferably of from about 85 to about 165 ns.

This synergistic interaction between the two wavelengths enhances the fragmentation effect of the long wavelength and enables its participation in the plasma sparking process at energy levels significantly below the threshold for plasma sparking experienced with this wavelength alone. The two wavelength pulses are administered in a manner which utilizes the minimum necessary energy in the SW pulse to initiate sparking in conjunction with moderate energy in the LW pulse to produce effective fragmentation. Because the plasma lifetime is short compared to the duration of the laser pulses, this process is most effective when the SW and LW laser pulses completely overlap. More desirably, the SW pulse should be timed to overlap the initial part of the LW temporal pulse, so as to initiate the plasma sparking before the LW pulse has achieved its intensity maximum. Therefore, tissue exposure by the potentially harmful short wavelength of laser light is thus minimized by primarily relying on the laser light in the long wavelength range to accomplish the fragmentation of calculi. One preferred embodiment of the present invention utilizes long wavelength coherent radiation of about 730-780 nm and short wavelength coherent radiation of about 365 -390 nm.

Briefly described, the apparatus of the present invention comprises a laser generating and delivering device, or devices, being capable of providing the above-mentioned two wavelengths at pulse energies, pulse durations, pulse temporal sequencing, and pulse repetition rates in accordance with the method of the present invention; and capable of delivering the two wavelengths substantially simultaneously to the targeted calcified matter. In the preferred embodiment, the apparatus comprises a Q-switched alexandrite laser generating light in the long wavelength spectrum and provided with a frequency doubling crystal for converting a portion of the output laser pulse into its second harmonic in the short wavelength spectrum. A focusing device coincidentally focuses both the LW and SW light at a selected point, which may be the calcified matter itself or, preferably, the collecting end of a fused silica fiber optic cable, by means of which the combined laser pulses are delivered to the calcified matter.

These and other objects, features and advantages of the present invention will become more readily apparent and understood upon reading and comprehending this specification in conjunction with the accompanying drawings.

BRIEF DESCRIPTION OF THE DRAWINGS

FIG. 6 summarizes comparative in vitro lithotripsy test results employing single frequency laser light at 504 nm;

FIG. 7 summarizes in vitro lithotripsy test results employing dual frequency (378 nm together with 755 nm) laser light in accordance with the invention.

DETAILED DESCRIPTION OF THE PREFERRED EMBODIMENT

Figure 1:
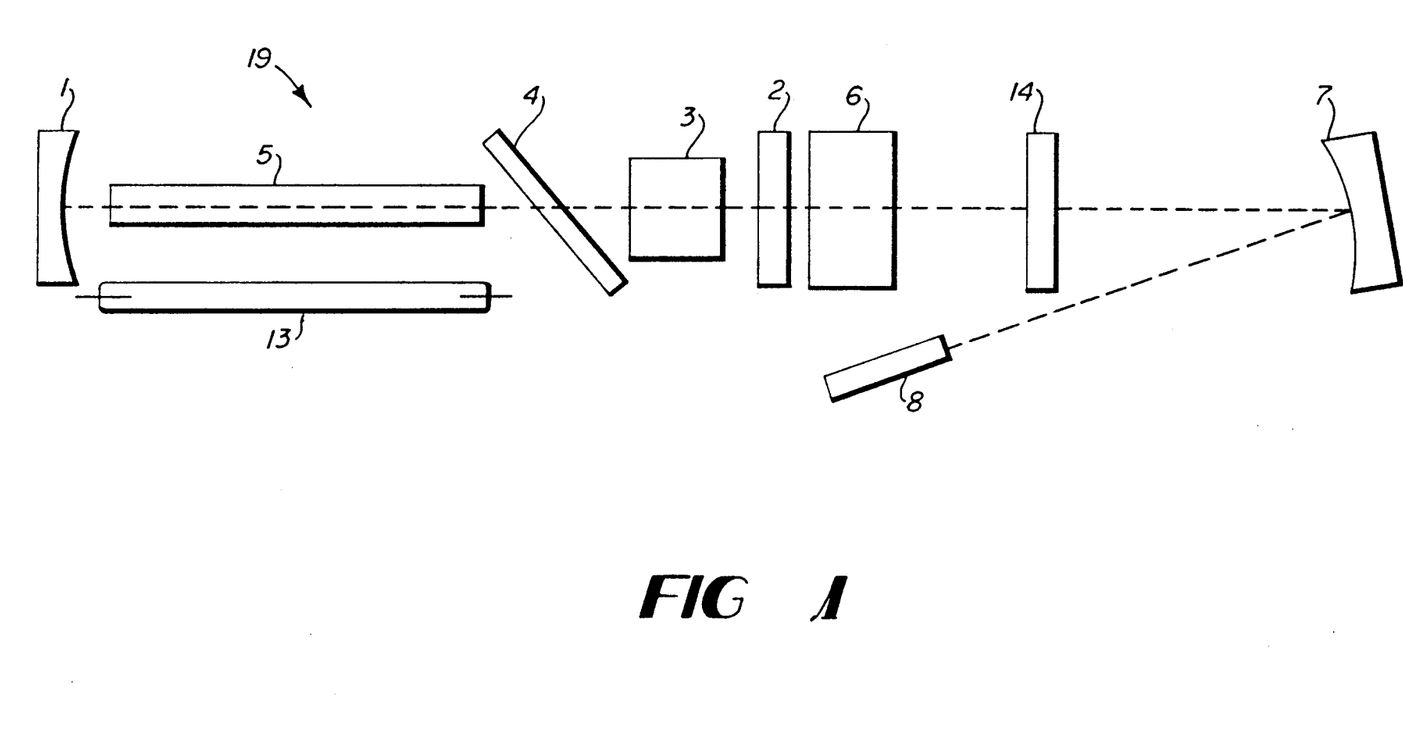
FIG. 1 is a schematic presentation of a dual wavelength lithotripter device of the present invention employing a single laser cavity.

Referring now in greater detail to the drawings in which like numerals represent like components throughout the several views, FIG. 1 shows a schematic representation of a dual wavelength lithotripter 19 in accordance with a preferred embodiment of the present invention. The preferred lasing medium is an alexandrite rod 5 which is a broadly tunable solid state chromium doped berylium aluminate material, such as is shown in U.S. Pat. Nos. 3,997,853 and 4,272,733, which are owned by Allied-Signal, Inc., Morristown, N.J. There are a variety of alternate laser materials that are capable of providing laser pulses of the desired characteristics: for example, Nd:BEL, Cr:GSGG, Ti:A1204, Ti:BeA1204, Cr:SrA1F5, excimer, ruby, emerald and dye lasers, whose output can be shifted using standard frequency shifting techniques to provide either the long or short wavelength laser energy.

A laser of the present invention is depicted schematically in FIG. 1. The laser comprises laser medium 5 in a resonant cavity defined by mirrors 1 and 2, of which 2 is partly reflecting (50% R typically). A Q-switch device 3 is provided in the cavity in order to provide a single high peak power laser pulse output (50-300 ns pulse) as is generally understood by those knowledgeable in the art. When medium 5 is excited by a conventional pulsed pump source 13, coherent radiation is emitted through mirror 2 as permitted by the intracavity Q-switch device 3 and passes through beam shifting means 6, which is typically a nonlinear mixing crystal of the type well known in the art. In a preferred embodiment, the present invention employs a beta barium borate frequency doubling crystal which provides greater than 15% conversion of the long wavelength output into the short wavelength spectrum. Thereafter, the beam, including the long and short wavelengths, passes to a front surface mirror 7 which coincidently focusses the two wavelengths into a beam delivery means 8, which may, for example, be a fiber optic cable. FIG. 1 also depicts a beam attenuator means 14 (i. e. neutral density filters, color filters, polarization) which may be used to selectively adjust the power ratio of the two wavelengths in the beam. Additionally, the coating applied to the focusing mirror 7 can be adjusted to provide the proper ratio of short to long wavelength pulse energy in the beam. Another optional device shown in FIG. 1 is an intracavity tuning device 4 which can be used to select a specific output wavelength from a broadly tunable lasing medium's emission bandwidth, such as alexandrite (720-790 nm), thus enhancing its beam shifting efficiency and interaction with target materials.

An example of the performance characteristics of a dual wavelength alexandrite laser system is as follows: a) an output of 0-200 mJ/pulse at 755 nm at 15 Hertz (Hz); b) a pulse width of the 755 nm output 100-300 ns full width half maximum (FWHM); c) a 15% doubling efficiency using beta barium borate to provide 0-30 mJ/pulse at 378 nm; d) 85 -245 ns pulse width at 378 nm FWHM; e) a focusing mirror 7 having a 50 millimeter (mm) focal length, which coincidently focusses the two laser output beams to a full beam diameter of less than 300 microns; and f) an intracavity 4-plate birefringent filter which provides tunable 0.1 nm bandwidth from 730-780 nm.

Figure 2:
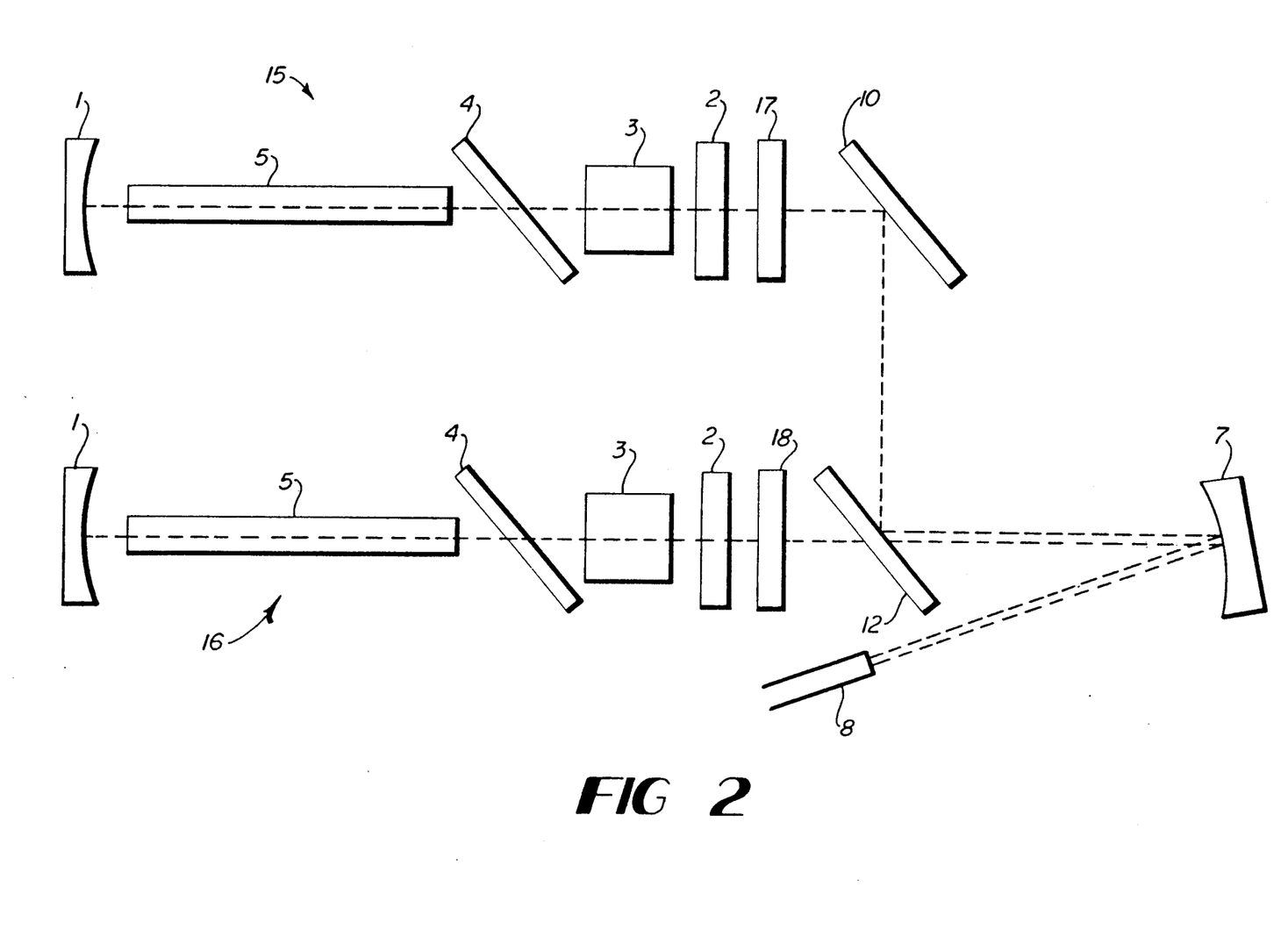
FIG. 2 is a schematic of a dual laser lithotripter system of the invention.

An alternate laser system for the embodiment of the present invention is depicted schematically in FIG. 2. In this device two laser systems 15 and 16 are employed to provide the laser pulses at the long and short wavelengths, respectively. In combination, the lasers of this embodiment function as the one described above, the difference being that the dual wavelengths (long and short) are created in two different laser systems. The laser output beams are combined with the aid of mirrors 10 and 12 which serve to spatially overlap the two beams into a single beam. These combined beams are then coincidentally focused by mirror 7 into the delivery means 8. Optionally, a means 17 and 18 (i.e. neutral density filters) is provided to selectively attenuate the individual laser beams to produce the desired ratio of long to short wavelength pulse energy. The temporal sequencing of these two laser pulses should follow the description provided in the text.

Figure 3:
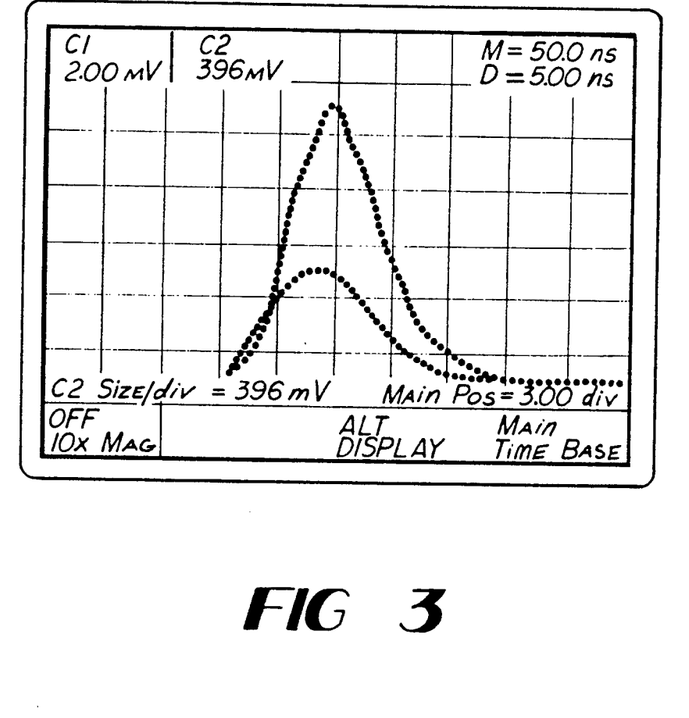
FIG. 3 is an oscilloscope trace of long and short wavelength laser pulses for laser lithotripsy in accordance with the invention.

In the preferred embodiment of the present invention, the most effective time sequencing of the laser pulses is shown in FIG. 3. This is a photograph of an oscilloscope trace of the two laser pulses temporal overlap, short (lower) and long (upper) wavelengths. The peak of the short wavelength pulse is achieved at about 15 nanoseconds (ns) before the peak of the long wavelength pulse. This sequencing scheme allows the plasma to ignite by the action of the short wavelength pulse before a significant part of the long wavelength pulse has irradiated the object calculi; and allows a significant part of the long wavelength pulse to irradiate the object calculi during the plasma lifetime. This is the most efficient use of the long wavelength pulse. Alternately, the long wavelength pulse may directly coincide temporally or even precede the short wavelength pulse but this would result in a diminished fragmentation efficiency of the target calculi.

Figure 4:
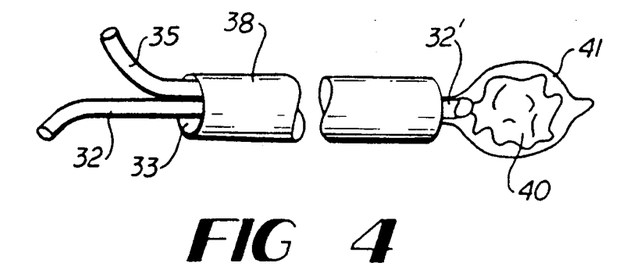
FIG. 4 is a schematic for an endoscope probe for delivering laser pulses.
Figure 5:
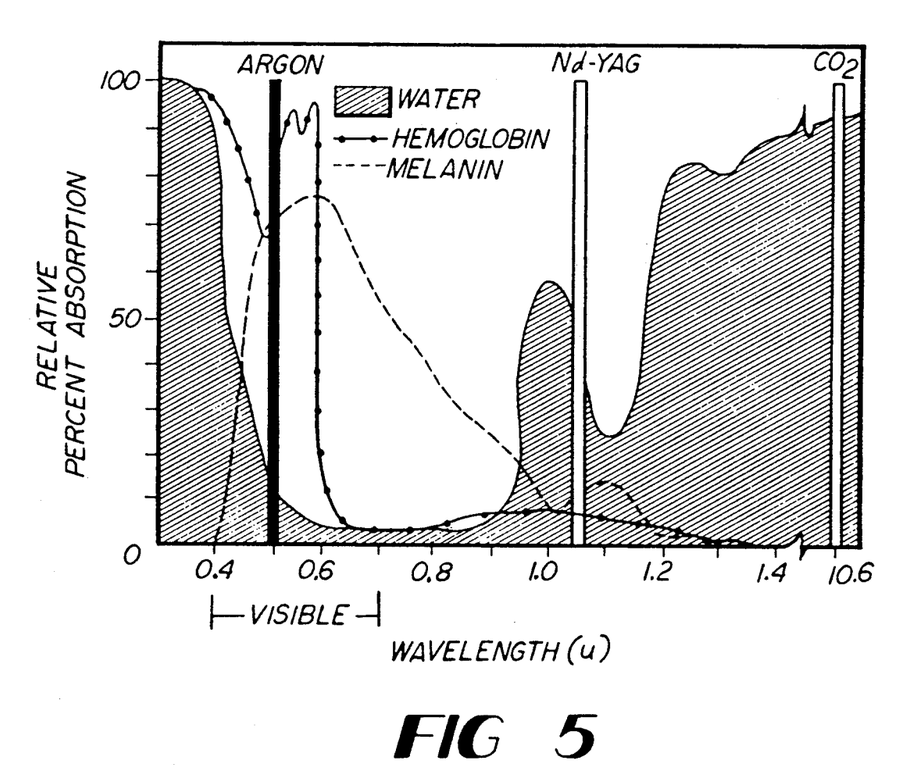
FIG. 5 shows the relative absorption in the light spectrum by water, hemoglobin and melanin.

The preferred embodiment of lithotripter 19 further comprises a fused silica fiber 32 or 200–400 micron core diameter. In the preferred embodiment and as best seen in FIG. 4, the fiber 32 is a 300 micron core fiber which is insertable into the working channel 33 of an endoscope or ureterescope 38 for positioning adjacent to the targeted calcified matter 40. A conventional stone basket may be employed to grasp the targeted matter 40 and hold it adjacent to the working end 32' of the optical fiber 32 so as to accurately aim the laser pulses into the matter 40. The endoscope 38 may also include a conventional irrigation channel 35.

In Vitro Test Results

To enable a direct comparison of fragmentation performance and test the concept of SW light acting as a plasma igniter in stones where LW light alone cannot generate consistent plasma sparking, eleven (11) specific samples of calculi were selected among a group of 47 different biliary and urinary calculi samples which composition had been previously analyzed.

These eleven (11) test samples were selected as those being extremely difficult or impossible to fragment when exposed to the 504 nm light of a commercially available dye laser lithotripter or to the 755 nm LW light of the Q-switched Alexandrite laser lithotripter.

In a series of experiments with a dual wavelength Alexandrite test laser substantially similar to the one described herein as a preferred embodiment and shown in FIG. 1, each of the eleven (11) calculi samples were irradiated with different energy levels of SW and LW light which were transmitted simultaneously through a tapered 500–300 micron fused silica fiber. Substantially enhanced fragmentation performance, as well as, the synergistic interaction of the SW and LW pulse components were clearly demonstrated.

For example, white Apatit & Struvite stone #KI-XI, in which little or no plasma sparking could be generated with up to 60 mJ of 504 nm light or up to 100 mJ of 755 nm LW light, responded very effectively to the combination of 4 mJ SW and 40 mJ LW light.

In the case of Cystine stone #KI-XVI, which did not respond at all to 60 mJ of 504 nm light or 100 mJ of 755 nm LW light, fragmentation was readily accomplished with a combination of 4 mJ of SW light and 32 mJ of LW light.

Removal of any of the two beam components during stone exposure, resulted in instant reduction of fragmentation response.

Further, the hard Brushite surface layer of stone #KDI-8, in which no plasma sparking at all could be obtained with 60 mJ of 504 nm light or 100 mJ of 755 nm LW light, responded with consistent plasma sparking when irradiated with 7 mJ SW and 52 mJ LW light.

The experiments with the eleven (11) different stone samples have established that the combination of 4–12 mJ of SW light and 15–35 mJ of LW light generates pulses which ensure consistent plasma sparking and fragmentation in most stones when delivered through a 300 micron fused silica fiber.

The table in FIG. 6 summarizes the specific fragmentation responses of the eleven (11) different stone samples to the 504 nm light of a commercially available dye laser lithotripter, at energy levels of between 30 and 60 mJ (a "prior art" method), as well as, the composition, color and surface structure of the samples.

The table in FIG. 7 summarizes the fragmentation response of the same eleven (11) stone samples, when tested with different levels of SW and LW light generated by the dual wavelength Alexandrite test laser, in accordance with the present invention, employing spatially and temporally overlapped short wavelength and long wavelength light. A stone by stone comparison of the fragmentation responses tabulated in FIG. 6 and FIG. 7, clearly demonstrates the superior and consistent performance of the invention method and apparatus.

Since various changes may be made in the invention without departing from its spirit and essential characteristics, it is intended that all matter contained in the description shall be interpreted as illustrative only and not in a limiting sense, the scope of the invention being defined by the appended claims.

We claim:

1. A laser lithotripter system comprising, in combination:
   a source of pulsed coherent radiation having a wavelength in the range of from about 300 to about 450 nm, at an energy level of from about 2 to about 30 mJ;
   a source of pulsed coherent radiation having a wavelength from about 600 to about 900 nm, at an energy level of from about 15 to about 100 mJ,
   said pulses of coherent radiation achieving temporal overlap; an endoscopic delivery system; and
   mirror means for focusing said temporally overlapping pulses of coherent radiation in spatially overlapped relationship into said endoscopic delivery system for delivery to calcified matter located within a mammalian body.

2. The laser lithotripter system of claim 1, wherein said source of pulsed coherent radiation having a wavelength in the range of from about 600 to about 900 nm comprises, at least, a first laser, and wherein said source of pulsed coherent radiation in the wavelength range of from about 300 to about 450 nm comprises, at least, means for frequency doubling the basic laser output of said first laser.

3. The laser lithotripter system of claim 2, wherein said frequency doubling means of said source of pulsed coherent radiation in the wavelength range of from about 300 to about 450 nm comprises, at least, a nonlinear crystal.

4. The laser lithotripter system of claim 2, further comprising, at least, a first Q-Switch device associated with said source of pulsed coherent radiation having a wavelength in the range of from about 600 to about 900 nm.

5. The laser lithotripter system of claim 4, further comprising at least a second Q-Switch device associated with said source of pulsed coherent radiation having a wavelength in the range of from about 300 to about 450 nm.

6. The laser lithotripter of claim 2, wherein said first laser is an alexandrite laser.

7. The laser lithotripter system of claim 1, wherein said endoscopic delivery system comprises, at least, a fiber-optic cable.

8. The laser lithotripter system of claim 1, wherein said mirror means comprises means for focusing said temporally overlapping pulses of coherent radiation in a completely spatially overlapped relationship into said endoscopic delivery system.

9. The laser lithotripter system of claim 1, wherein said mirror means comprises, at least, a front surface mirror.

10. The laser lithotripter system of claim 1, wherein said source of pulsed coherent radiation having a wavelength in the range of from about 600 to about 900 nm comprises, at least, a first laser, and wherein said source of pulsed coherent radiation in the wavelength range of from about 300 to about 450 nm comprises, at least, an independent, second laser.

11. A method for fragmentation of calcified matter in the mammalian body, which method comprises the steps of:
  initiating plasma sparking in the calcified matter by subjecting the surface of the calcified matter to a first beam having a wavelength in the range of from about 300 nanometers to about 450 nanometers; and
  subjecting the calcified matter to a second beam having a wavelength in the range of from about 600 nanometers to about 900 nanometers, the second beam spatially and temporally overlapping the first beam.

12. Method of claim 11, wherein the step of subjecting the calcified matter to a second beam comprises, at least, the step of:
  subjecting the calcified matter to a second beam having a wavelength in the range of from about 600 nanometers to about 900 nanometers, the second beam being spatially and temporally coincident with the first beam.

13. The method of claim 11, wherein said first and second beams are pulsed.

14. The method of claim 13, wherein the initiating step further comprises the step of subjecting the calcified matter to a first beam having an energy level in the range of from about 2 to about 30 mJ; and wherein the subjecting step further comprises the step of subjecting the calcified matter to a second beam having an energy level of about 15 to about 100 mJ.

15. The method of claim 14, wherein the mammalian body is a human, and wherein the initiating step further comprises the step of subjecting the calcified body to a first beam having pulse durations of from about 50 nanoseconds (ns) to about 300 ns, and wherein the subjecting step further comprises the step of subjecting the calcified body to a second beam having pulse durations of from about 50 nanoseconds (ns) to about 300 ns.

16. The method of claim 11, wherein the mammalian body is a human body.

17. The method of claim 11, wherein the mammalian body is a human body, and wherein the method further comprises the steps of generating the second beam by a laser, and frequency doubling at least a portion of the second beam to create the first beam.

18. The method of claim 17, wherein the step of generating the second beam by a laser comprises the step of generating the second beam by an alexandrite laser.

19. The method of claim 17, wherein the step of generating the second beam further comprises the step of Q-switching the laser; and wherein the method further comprises the steps of:
  developing the first and second beams with energy levels in the range of from about 2 to about 30 mJ and of from about 15 to about 100 mJ, respectively; and
  developing the first and second beams with pulse durations of from about 50 nanoseconds (ns) to about 300 ns.

20. The method of claim 17, wherein the generating step further comprises the step of generating the first beam with a wavelength in the range of from about 365 nm to about 390 nm; and
  generating the second beam with a wavelength of from about 730 nm to about 780 nm.

21. The method of claim 11, wherein the mammalian body is a human body, and wherein the method further comprises the steps of generating the first beam by a first laser and generating the second beam by an independent second laser.

22. The method of claim 21, wherein the step of generating the first beam further comprises the steps of:
  Q-switching the first laser;
  generating the first beam with energy levels in the range of from about 2 to about 30 mJ; and
  generating the first beam with pulse durations of from about 50 nanoseconds (ns) to about 300 ns; and wherein the step of generating the second beam further comprises the steps of:
  Q-switching the second laser;
  generating the second beam with energy levels in the range of from about 15 to about 100 mJ; and
  generating the second beam with pulse durations of from about 50 nanoseconds (ns) to about 300 ns.

23. The method of claim 21, wherein the generating steps further comprises the steps of:
  generating the first beam with a wavelength in the range of from about 365 nm to about 390 nm; and
  generating the second beam with a wavelength of from about 730 nm to about 780 nm.

24. The method of claim 21, wherein the step of generating the second beam comprises the step of generating the second beam by an independent, alexandrite laser.

25. A method of fragmentation of calcified matter in the mammalian body, which method comprises the steps of:
  initiating plasma sparking in the calcified matter and creating an acoustic wave by subjecting the surface of the calcified matter to a first beam having a wavelength in the range of from about 300 nanometers to about 450 nanometers; and
  subjecting the calcified matter to a second beam having a wavelength in the range of from about 600 nanometers to about 900 nanometers, the energy of the second beam being absorbed by the plasma and thereby amplifying the plasma sparking, whereby the calcified matter is fragmented.

26. Method of claim 25, wherein the step of subjecting the calcified matter to a second beam comprises, at least, the step of:
  subjecting the calcified matter to a second beam having a wavelength in the range of from about 600 nanometers to about 900 nanometers, the second beam being spatially and temporally coincident with the first beam.

27. The method of claim 25, wherein said first and second beams are pulsed.

28. The method of claim 27, wherein the initiating step further comprises the step of subjecting the calcified matter to a first beam having an energy level in the range of from about 2 to about 30 mJ; and wherein the subjecting step further comprises the step of subjecting the calcified matter to a second beam having an energy level of about 15 to about 100 mJ.

29. The method of claim 28, wherein the mammalian body is a human, and wherein the initiating step further comprises the step of subjecting the calcified body to a first beam have pulse durations of from about 50 nanoseconds (ns) to about 300 ns, and wherein the subjecting step further comprises the step of subjecting the calcified body to a second beam have pulse durations of from about 50 nanoseconds (ns) to about 300 ns.

30. The method of claim 25, wherein the mammalian body is a human body.

31. The method of claim 25, wherein the mammalian body is a human body, and wherein the method further comprises the steps of generating the second beam by a laser, and frequency doubling at least a portion of the second beam to create the first beam.

32. The method of claim 31, wherein the step of generating the second beam by a laser comprises the step of generating the second beam by an alexandrite laser.

33. The method of claim 31, wherein the step of generating the second beam further comprises the step of Q-switching the laser; and wherein the method further comprises the steps of:

developing the first and second beams with energy levels in the range of from about 2 to about 30 mJ and of from about 15 to about 100 mJ, respectively; and developing the first and second beams with pulse durations of from about 50 nanoseconds (ns) to about 300 ns.

34. The method of claim 31, wherein the generating step further comprises the step of generating the first beam with a wavelength in the range of from about 365 nm to about 390 nm; and generating the second beam with a wavelength of from about 730 nm to about 780 nm.

35. The method of claim 25, wherein the mammalian body is a human body, and wherein the method further comprises the steps of generating the first beam by a first laser and generating the second beam by an independent second laser.

36. The method of claim 35, wherein the step of generating the first beam further comprises the steps of:

Q-switching the first laser;

generating the first beam with energy levels in the range of from about 2 to about 30 mJ; and generating the first beam with pulse durations of from about 50 nanoseconds (ns) to about 300 ns; and wherein the step of generating the second beam further comprises the steps of:

Q-switching the second laser;

generating the second beam with energy levels in the range of from about 15 to about 100 mJ; and generating the second beam with pulse durations of from about 50 nanoseconds (ns) to about 300 ns.

37. The method of claim 35, wherein the generating steps further comprise the steps of:

generating the first beam with a wavelength in the range of from about 365 nm to about 390 nm; and generating the second beam with a wavelength of from about 730 nm to about 780 nm.

38. The method of claim 35, wherein the step of generating the second beam comprises the step of generating the second beam by an independent, alexandrite laser.

* * * * *